(12) United States Patent
Bosel

(10) Patent No.: US 9,808,333 B2
(45) Date of Patent: Nov. 7, 2017

(54) SPLITTABLE SHEATH

(71) Applicant: Cook Medical Technologies LLC, Bloomington, IN (US)

(72) Inventor: Christopher D. Bosel, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 598 days.

(21) Appl. No.: 13/627,449

(22) Filed: Sep. 26, 2012

(65) Prior Publication Data
US 2014/0088608 A1 Mar. 27, 2014

(51) Int. Cl.
*A61F 2/06* (2013.01)
*A61B 17/11* (2006.01)

(52) U.S. Cl.
CPC .............. *A61F 2/064* (2013.01); *A61B 17/11* (2013.01); *A61B 2017/1103* (2013.01); *A61B 2017/1107* (2013.01); *A61B 2017/1132* (2013.01)

(58) Field of Classification Search
CPC . A61F 2/97; A61F 2/064; A61B 17/11; A61B 2017/1132; A61B 2017/1107; A61B 2017/1103
See application file for complete search history.

(56) References Cited

U.S. PATENT DOCUMENTS

| | | | |
|---|---|---|---|
| 4,306,562 A | 12/1981 | Osborne | 128/348 |
| 4,581,025 A | 4/1986 | Timmermans | 604/264 |
| 5,647,857 A * | 7/1997 | Anderson | A61F 2/958 604/160 |
| 7,766,953 B2 | 8/2010 | Purdy et al. | 623/1.12 |
| 2007/0027526 A1 | 2/2007 | Demetriades et al. | 623/1.13 |
| 2007/0198077 A1 | 8/2007 | Cully et al. | 623/1.12 |
| 2008/0132879 A1* | 6/2008 | Rasmussen | A61F 2/97 604/526 |
| 2009/0254168 A1 | 10/2009 | Parker et al. | 623/1.11 |
| 2012/0035706 A1 | 2/2012 | Paul, Jr. et al. | 623/1.12 |
| 2012/0035708 A1 | 2/2012 | Paul, Jr. et al. | 623/1.16 |
| 2012/0046652 A1* | 2/2012 | Sokel | A61F 2/95 606/1 |
| 2012/0123511 A1 | 5/2012 | Brown | 623/1.11 |
| 2012/0271400 A1 | 10/2012 | Lyons et al. | 623/1.12 |
| 2012/0271402 A1 | 10/2012 | Sargent, Jr. | 623/1.15 |
| 2013/0041451 A1* | 2/2013 | Patterson et al. | 623/1.12 |

* cited by examiner

Primary Examiner — Katherine M Shi
Assistant Examiner — Michael Mendoza
(74) Attorney, Agent, or Firm — Brinks Gilson & Lione

(57) ABSTRACT

A sheath for retaining a prosthesis for use in repair of a damaged portion of a body vessel during an open surgical procedure. The prosthesis is of a type having a constricted condition for delivery to the damaged vessel portion and an expanded condition upon deployment from the sheath. The sheath includes a generally cylindrical body having a distal end portion, a proximal end portion, a passageway extending therethrough, and an elongated tab member at the proximal end portion. The tab member is positionable along the generally cylindrical body for initiating the splitting of the generally cylindrical body from the distal end portion of the sheath body toward the proximal end portion.

20 Claims, 4 Drawing Sheets

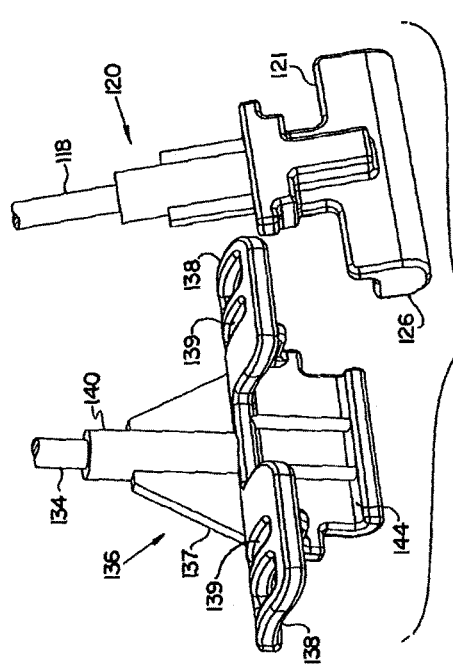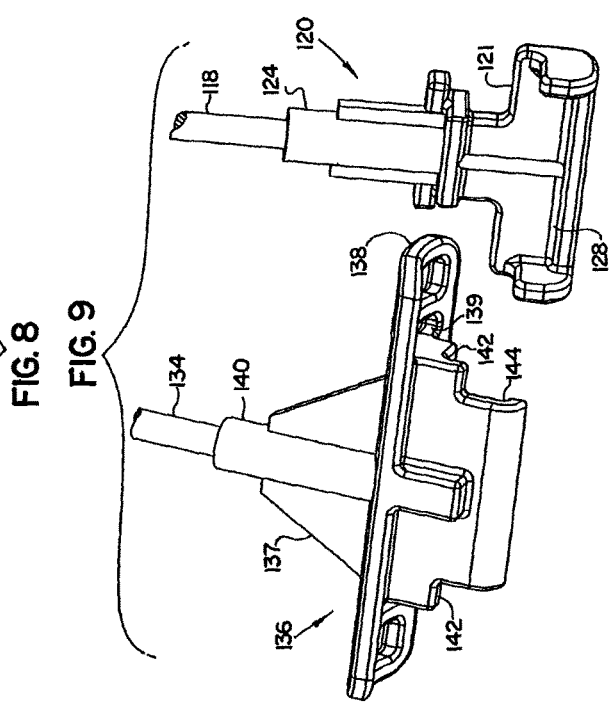

SPLITTABLE SHEATH

BACKGROUND

1. Technical Field

The present invention relates generally to a sheath for use in constraining a medical interventional device upon delivery to a body vessel in need of repair. More particularly, the invention relates to a splittable sheath for use in constraining an end of an expandable prosthesis upon insertion of the prosthesis into a damaged body vessel during an open surgical medical procedure.

2. Background Information

Trauma physicians frequently encounter patients having traumatic injury to a body vessel, such as lacerated vessels or even transected vessels, resulting from gunshots, knife wounds, motor vehicle accidents, explosions, etc. Significant damage to a body vessel may expose a patient to deleterious conditions such as the loss of a limb, loss of function of a limb, increased risk of stroke, impairment of neurological functions, and compartment syndrome, among others. Particularly severe cases of vascular injury and blood loss may even result in death. In such severe situations, the immediate goal is to obtain hemostasis while maintaining perfusion of adequate blood flow to critical organs, such as the brain, liver, kidneys, and heart.

Examples of treatment that are commonly performed by trauma physicians to treat body vessel injuries include the clamping of the vessel with a hemostat, the use of a balloon tamponade, the ligation of the damaged vessel at or near the site of injury, and/or the insertion of one or more temporary shunts. However, conventional surgical repair is generally difficult with actively bleeding, moribund patients. In many instances, there is not enough time to repair the body vessel adequately by re-approximating and suturing the body vessel. Thus, the trauma physician may simply insert a temporary shunt into the vessel. However, use of temporary shunts has been linked to the formation of clots. This may require returning the patient to the operating room for treatment and removal of the clots, often within about 36 to 48 hours of the original repair. Since such shunts are generally placed as a temporary measure to restore blood flow and stop excessive blood loss, the shunt is typically removed by a specialized vascular surgeon once the patient has stabilized (generally a few days later). After removal, the vascular surgeon will typically replace the shunt with a vascular graft, such as a fabric graft that is sewn into place. With respect to ligation, ligation of the damaged blood vessel may result in muscle necrosis, loss of muscle function, or a potential limb loss or death.

Due to the nature of the body vessel injury that may be encountered, the insertion of shunts or ligation of a blood vessel, for example, often requires that such treatments be performed within a very short period of time. Such treatments may occupy an undue amount of time and attention of the trauma physician at a time when other pressing issues regarding the patient's treatment require immediate attention. In addition, the level of particularized skill required to address a vascular trauma and stabilize the patient may exceed that possessed by the typical trauma physician.

Some open surgical techniques utilize sutures to affix damaged tissue portions to fittings that have been deployed with the vessel. Such techniques require the trauma physician to take sufficient time to tie the sutures properly. Even though in modern medicine sutures can be tied in relatively rapid fashion, any step in a repair process that occupies physician time in an emergency situation is potentially problematic. In addition, the use of sutures to affix the vessel to the fitting compresses the tissue of the vessel against the fitting. Compression of tissue may increase the risk of necrosis of the portion of the vessel tissue on the side of the suture remote from the blood supply. When present, necrosis of this portion of the vessel tissue may result in tissue separation at the point of the sutures. In this event, the connection between the vessel and the fitting may eventually become weakened and subject to failure. If the connection fails, the device may disengage from the vessel. Therefore, efforts continue to be made to develop suitable techniques that reduce the physician time required for such repair, so that this time can be spent on other potentially life-saving measures, and so that the blood flow may be more quickly restored and any resulting damage caused by lack of blood flow is minimized.

A device and a method for delivering a prosthesis for use in repair of a damaged body vessel during emergency open surgery are disclosed in my co-pending U.S. patent application Ser. No. 13/627,428, filed Sep. 26, 2012, titled "Delivery Device and System for Open Surgical Repair". This document is incorporated by reference herein in its entirety. The incorporated-by-reference document discloses a device useful for delivering a prosthesis into a damaged body vessel, wherein each end of the prosthesis is constrained in a separate sheath upon insertion into the vessel. Once the sheaths and the prosthesis are positioned in the vessel, each sheath is split such that the respective ends of the prosthesis expand in the vessel. Barbs or other anchoring members at the ends of the prosthesis penetrate the vessel wall to anchor the prosthesis in the vessel. The intermediate length of the prosthesis bridges the damaged vessel portion to enable restoration of blood flow therethrough.

Splittable sheaths are well known in the medical arts. Examples of such sheaths are described, e.g., in U.S. Pat. No. 4,306,562 to Osborne and U.S. Pat. No. 4,581,025 to Timmermans, each of which is incorporated herein by reference in its entirety. Typically, prior art sheaths include one or more tab members that are pulled by the physician, often utilizing a needle holder or other clamping tool, to cause the sheath body to split in a longitudinal direction. With some prior art sheaths, as the tab and an accompanying sheath portion are withdrawn from the vessel, a portion of the sheath on the opposite side of the split line remains in the vessel. Following expansion of the prosthesis, this portion must also be removed from the vessel. Typically, this remaining sheath portion is captured by the physician utilizing a tool as described above, and thereafter removed from the vessel.

In order to facilitate withdrawal of the remaining sheath portion, a sheath in the incorporated-by-reference patent application cited above may utilize dual tabs. One tab is utilized for the initial splitting and removal of the sheath portion as described above. The other tab is associated with the remaining portion of the sheath. This tab provides a readily accessible target for the physician, and the sheath portion may be removed following expansion of the prosthesis by re-inserting the tool, capturing the tab, and withdrawing the tab and remaining sheath portion from the vessel. However, this dual-tab sheath does not eliminate a necessity to return to the vessel to remove a remaining portion of the sheath following the splitting and removal of an initial sheath portion.

It is desired to provide a modified sheath for use with an expandable prosthesis. It is further desired to provide a sheath for use with an expandable prosthesis during emergency open surgical procedures, in which the sheath is splittable and fully removable by the physician from the vessel and a prosthesis by pulling a single tab.

BRIEF SUMMARY

The problems of the prior art are addressed by the features of the present invention. In one aspect, a sheath is disclosed for retaining a prosthesis of a type having a constricted condition for delivery to a damaged portion of a body vessel, and an expanded condition upon deployment from the sheath at the damaged vessel portion. The sheath comprises a generally cylindrical body having a distal end portion, a proximal end portion, a passageway extending therethrough, and an elongated tab member engaged at the proximal end portion. The tab member is positionable along the generally cylindrical body for initiating a splitting of the generally cylindrical body from the distal end portion toward the proximal end portion.

In another aspect, an assembly is disclosed for open surgical repair of a damaged portion of a body vessel. The assembly comprises a prosthesis having a first end and a second end, the prosthesis being expandable from a constricted condition wherein at least the first and second ends have a diameter less than a diameter of the body vessel at the damaged portion, to an expanded condition wherein the prosthesis ends engage an interior surface of the body vessel. A first splittable sheath maintains the prosthesis first end in the constricted condition. The first splittable sheath comprises a generally cylindrical body having a distal end portion, a proximal end portion, a passageway extending therethrough, and an elongated tab member engaged at the proximal end portion. The tab member is positionable along the generally cylindrical body for initiating a splitting of the generally cylindrical body of the first splittable sheath from the distal end portion toward the proximal end portion. A second splittable sheath maintains the prosthesis second end in the constricted condition. The second splittable sheath comprises a generally cylindrical body having a distal end portion, a proximal end portion, a passageway extending therethrough, and an elongated tab member engaged at the proximal end portion. The tab member is positionable along the generally cylindrical body for initiating a splitting of the generally cylindrical body of the second splittable sheath from the distal end portion toward the proximal end portion.

In yet another aspect, a method for open surgical repair of a damaged portion of a body vessel is disclosed. A device having a prosthesis loaded therein is positioned for delivery to the damaged vessel portion through an open air pathway. The prosthesis has a first end and a second end, and is expandable from a constricted condition wherein at least the first and second ends have a diameter less than a diameter of the body vessel at the damaged portion, to an expanded condition. A first sheath maintains the prosthesis first end in the constricted condition, and a second sheath maintains the prosthesis second end in the constricted condition. Each of the sheaths comprises a generally cylindrical body having a distal end portion, a proximal end portion, a passageway extending therethrough, and an elongated tab member engaged at the proximal end portion. The tab member is positionable along the generally cylindrical body for initiating a splitting of the generally cylindrical body from the distal end portion toward the proximal end portion. An end of the delivery device is advanced through the open air pathway to damaged body vessel portion with the prosthesis ends in the constricted condition. The delivery device and the first sheath are maneuvered such that the first constricted prosthesis end is inserted at a first side of the damaged body vessel portion. The first sheath tab member is pulled for splitting the first sheath from the distal end portion to the proximal end portion such that the prosthesis first end expands to engage an interior surface of the body vessel. The delivery device and the second sheath are maneuvered such that the second constricted prosthesis end is inserted at a second side of the damaged body vessel portion. The second sheath tab member is pulled for splitting the second sheath from the distal end portion to the proximal end portion such that the prosthesis second end expands to engage an interior surface of the body vessel. The first sheath may be removed by withdrawing the first sheath tab member, and the second sheath may be removed by withdrawing the second sheath tab member.

BRIEF DESCRIPTIONS OF THE DRAWINGS

FIG. 8 is a view of the distal end of the delivery device of FIG. 7, illustrating the retaining members of the delivery device in an open position;

FIG. 9 is another view of the distal end of the delivery device, showing an opposite rotational orientation of the retaining members when compared to FIG. 8;

DETAILED DESCRIPTION OF THE DRAWINGS AND THE PRESENTLY PREFERRED EMBODIMENTS

Figure 1:
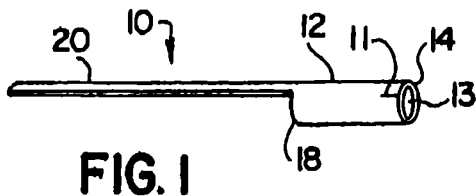
FIG. 1 is a side view of a sheath according to the present invention, wherein the tab member of the sheath is oriented in an initial condition.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. It is understood that like-referenced numerals are used throughout the Figures to designate similar components.

Throughout the specification, when referring to a medical device, or a portion of a medical device, the terms "distal" and "distally" shall denote a position, direction, or orientation that is generally towards, or in the direction of, the patient when the device is in use, and/or to a portion of the medical device that is initially inserted into a body vessel of the patient. The terms "proximal" and "proximally" shall denote a position, direction, or orientation that is generally away from the patient, and/or closer to the operator, during use of the device.

The sheath described herein can be utilized to constrain a prosthesis that is implanted for repair of body structures that define lumens, ducts, or passageways of the body, with the term "body vessel" used in the specification to describe these structures in general. In one example, the prosthesis can be deployed for repair of a lacerated or transected body vessel during emergency open surgical repair. In another example, the prosthesis can be deployed for implantation during bypass surgery.

FIGS. 1-6 illustrate one example of a sheath 10 that may be utilized to constrain a prosthesis, or a segment of a prosthesis, as the prosthesis is implanted within a body vessel. Sheath 10 includes a generally cylindrical sheath body 12 having a distal end portion 14, a proximal end portion 18, and a passageway 13 extending therethrough. An elongated tab member 20 extends from sheath body 12, such as from sheath body proximal end portion 18 as shown. The distal end may be pre-weakened in a conventional manner to initiate splitting. In the example shown in the figures, the distal end is pre-weakened by cutting a small slit 11 in the proximal direction from distal end portion 14.

Figure 4:
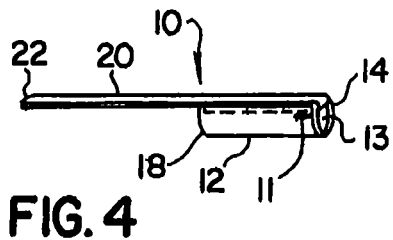
FIG. 4 is a side view of the sheath of FIG. 1, wherein the tab member is oriented in a condition for splitting.
Figure 2:
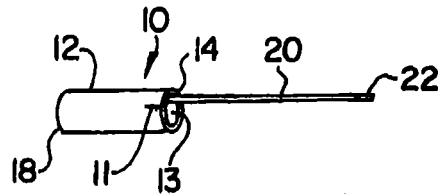
FIG. 2 is a side view of the sheath of FIG. 1, wherein the tab member is oriented in an intermediate condition.
Figure 6:
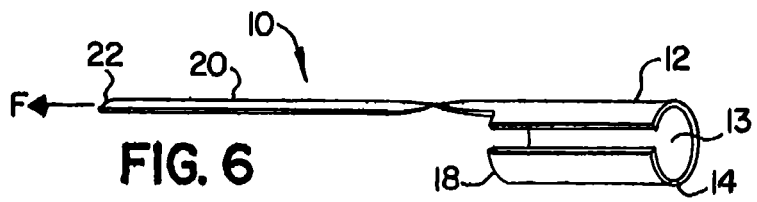
FIG. 6 is a side view of the sheath of FIG. 1 following splitting of the sheath body.

FIGS. 1, 2, and 4 illustrate side views of sheath 10. The views of the respective figures differ resulting from a manipulation of elongated tab member 20 in a manner further described herein. FIG. 6 is a side view of the sheath following splitting by drawing tab member 20 in a proximal direction, as further described herein.

FIG. 1 is a side view of sheath 10 in an initial condition, that is, prior to a manipulation of the elongated tab member into condition to split the sheath. As shown in this figure, elongated tab member 20 is integral with, and extends longitudinally from, proximal end 18 of sheath body 12.

Figure 3:
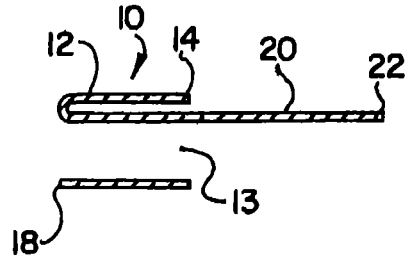
FIG. 3 is a longitudinal sectional view of the sheath as shown in FIG. 2.

FIG. 2 illustrates a side view of sheath 10, in an intermediate condition. In this condition, elongated member 20 has been folded over and threaded through sheath interior passageway 13 such that an end portion 22 of elongated tab member 20 is positioned distal of sheath body 12. FIG. 3 is a longitudinal sectional view of sheath 10 in the intermediate condition shown in FIG. 2.

Figure 5:
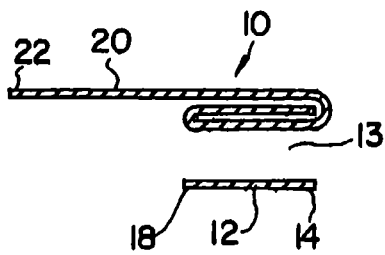
FIG. 5 is a longitudinal sectional view of the sheath as shown in FIG. 4.

FIG. 4 illustrates a side view of sheath 10 in condition for splitting. In this condition, tab member 20 has been folded over a second time such that end portion 22 extends proximal of sheath body 12, and is generally parallel to the axis of sheath body 12. FIG. 5 is a longitudinal sectional view of sheath 10 in the condition shown in FIG. 4. Typically, the prosthesis is inserted into sheath 10 when the sheath is in the condition shown in FIGS. 4 and 5.

Splittable sheaths for maintaining a prosthesis in a constricted, or compressed, condition prior to deployment at a target site are known in the art, such as in the incorporated-by-reference U.S. Pat. No. 4,306,562 and U.S. Pat. No. 4,581,025. As shown in the prior art sheaths, a tab member at the proximal end of the sheath is pulled, whereby the sheath splits in a generally longitudinal fashion from the proximal end to the distal end of the sheath.

As the tab member(s) of such prior art sheaths are withdrawn or pulled in the proximal direction, the distal end of the sheath has a tendency to be pulled in the proximal direction prior to splitting. In this event, friction between the respective sheath and compressed prosthesis may result in the prosthesis being pulled in the proximal direction along with the overlying sheath portion. When this occurs, the prosthesis may be undesirably displaced in the proximal direction from its optimal position. Depending upon the amount of displacement, the prosthesis may need to be re-positioned. In some instances, it may be necessary to re-start the overall process, and re-deploy a prosthesis from another sheath.

With the sheath 10 illustrated in FIGS. 1-6, as end portion 22 of the elongated tab member is pulled in the proximal direction, the initial split occurs at the distal end 14 of the sheath. In the example shown, slit 11 is a starting point for the splitting process. When the end of the tab member is pulled parallel to the axis of the sheath body in the proximal direction, the force F (FIG. 6) exerted by the tab member on the sheath body causes the sheath to initially split from the pre-weakened slit portion. The split then sequentially extends along the sheath body from the distal end to the proximal end. Once the sheath body has been split to the proximal end, the sheath body is now entirely split along one side. The sequence of splitting the sheath body 12 is best visualized upon a comparison of the pre-split condition of FIG. 4 with the split condition of FIG. 6.

After sheath body 12 has been completely split, the tab member remains attached to the sheath body, although now twisted 360 degrees from the former orientation, as shown in FIG. 6. Exertion of a continued force F on the tab member end causes the opened sheath body to pull away from the prosthesis, whereupon it is pulled from the vessel. In this arrangement there is considerably less friction between the sheath and the prosthesis when compared to that of the prior art structure, thereby allowing the sheath to be pulled proximally for removal from the vessel without pulling the prosthesis as well. Additionally, as further described herein, since anchoring members of the prosthesis are typically engaged with the vessel, further movement of the prosthesis in the proximal direction is inhibited for this additional reason.

Figure 7:
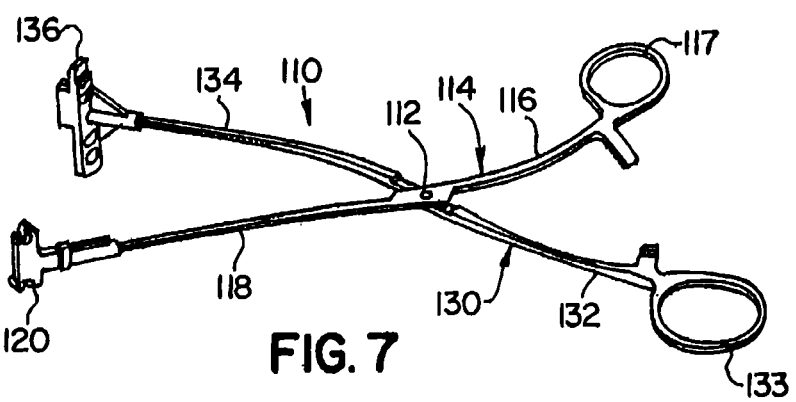
FIG. 7 illustrates one example of a delivery device for delivering a prosthesis for implantation within a body vessel.

The structure and use of sheath 10 can be further understood by the description of the following example, and as shown in the accompanying figures. This example describes the deployment of a prosthesis into a damaged body vessel, such as a lacerated or a transected vessel. One example of a suitable delivery device 110 is shown in FIG. 7. In this example, delivery device 110 includes a pair of elongated members 114, 130 movably joined to each other in known manner, such as at a pivot point 112. Elongated members 114, 130 include respective proximal ends 116, 132 and distal ends 118, 134. Proximal ends 116, 132 can include respective finger loops 117, 133 to facilitate grasping and control of the device by the operator. Delivery device 110 is further described in incorporated-by-reference Delivery Device and System for Open Surgical Repair patent application cited above.

A retaining member suitable for receiving a medical interventional device, such as a prosthesis, for implantation may be provided at each distal end. As shown in FIG. 7, retaining member 120 is provided at distal end 118, and retaining member 136 is provided at distal tip end 134. Retaining members 120, 136 are cooperatively sized and shaped to retain the prosthesis therebetween as the prosthesis is delivered to the target site. In the orientation shown in FIG. 7, the retaining members 120, 136 are spaced in an open position.

Retaining members 120, 136 of delivery device 110 are shown in FIGS. 8 and 9. In each of the rotational orientations shown in the figures, each retaining member is spaced from the other retaining member a distance that approximates the open position of device 110 illustrated in FIG. 7. Retaining member 136 comprises a generally rigid wall member 137 having a pair of wings 138 projecting in a transverse direction therefrom. An aperture 139 in each wing 138 is situated to receive elongated tab member 20 of sheath 10, as shown herein. Wall member 137 also includes a generally cylindrical portion 140 having a bore therein for receiving elongated member distal end 134. Retaining member 136 also includes arms 142 and ledge 144. Arms 142 and ledge 144 assist in the alignment of the prosthesis in the delivery device.

Retaining member 120 comprises generally rigid cradle member 121. Retaining member 120 includes a generally cylindrical portion 124 having a bore therein for receiving elongated member distal end 118. Cradle member 121 includes arms 126 and ledge 128. As shown, the respective arms 126, 142 and ledges 128, 144 of retaining members 120, 136 are sized and spaced to retain the prosthesis when the delivery device is in a closed position prior to deployment at the target site.

Figure 10:
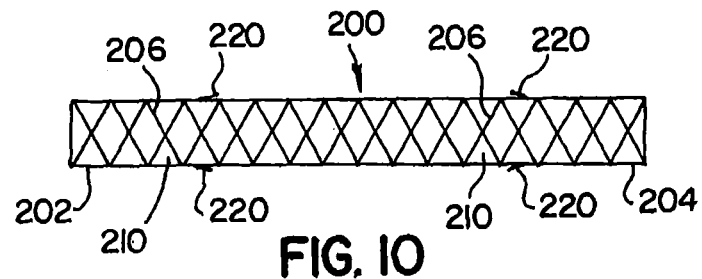
FIG. 10 is a side view of a radially expanded prosthesis suitable for deployment at a target site by the delivery device of FIG. 7.

FIG. 10 illustrates one example of a prosthesis 200 that may be deployed at the target site via delivery device 110. Prosthesis 200 may be a conventional stent/graft device of a type known in the art for implantation in a body vessel. In the example shown, prosthesis 200 includes stent 206 overlying graft body 210. Anchoring members, such as barbs 220, are circumferentially spaced along the length of the prosthesis in the vicinity of the proximal and distal ends 202, 204 of the prosthesis, for anchoring the prosthesis in the body vessel. The prosthesis is expandable between a radially compressed, delivery configuration (FIG. 11), and a radially expanded, deployed configuration (FIG. 10). Further description of a prosthesis is provided in the incorporated-by-reference patent application. Other examples of suitable prostheses are described in U.S. Pat. Appl. Publ. Nos. 2012/0035708 and 2012/0035706, incorporated herein by reference in their entireties.

Figure 11:
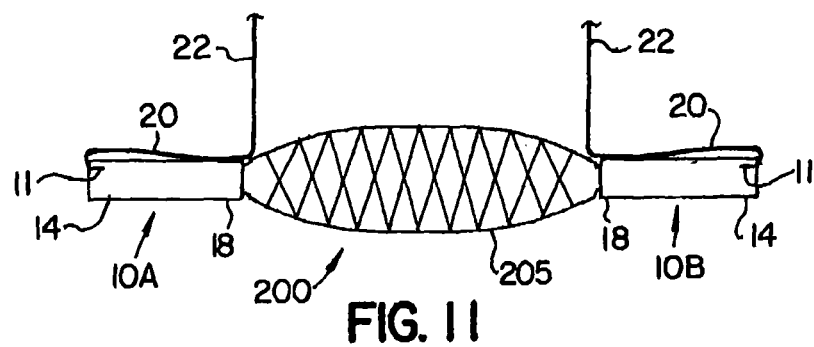
FIG. 11 is a side view of the prosthesis in condition for deployment, wherein each end of the prosthesis is constricted in a splittable sheath.

FIG. 11 illustrates a respective sheath 10A, 10B loaded onto each of the proximal and distal ends of prosthesis 200. As shown, each end 202, 204 of the prosthesis is constricted and maintained in a respective sheath. An intermediate length 205 of prosthesis 200 between proximal and distal ends 202, 204 is not otherwise constrained. Those skilled in the art will appreciate that prosthesis 200 has a length suitable for bridging a damaged area of tissue in the body vessel, as further described herein. For example, the prosthesis may have a length between about 40 and 100 mm, and more typically between about 50 and 70 mm. With a prosthesis of about 50 to 70 mm, approximately 10-12 mm at each axial end of the prosthesis is retained in constricted form in a respective sheath 10A, 10B, for insertion into a respective vessel end.

Sheaths 10A, 10B can be made of any biocompatible material that is suitable for retaining the prosthesis end in a radially constricted condition, and yet is still capable of being split and/or peeled from the prosthesis as described above. It is generally preferred to form the sheath from materials that are as thin as possible to reduce the overall delivery profile of the sheath. The sheath is preferably configured to be separated in a generally longitudinal manner along a relatively predictable path as shown in FIG. 6. In one example, the sheath can comprise a splittable polymer such as a molecularly oriented polytetrafluoroethylene (PTFE). One example of a sheath formed from such a polymer is the PEEL-AWAY® Sheath, commercially available from Cook Medical Incorporated, of Bloomington, Ind. Other examples are described in the aforementioned U.S. patents. Splittable sheaths are known in the medical arts, and the skilled artisan may readily select other known compositions suitable for use herein.

Preferably a sheath used herein will have a length at least as long as the length of the constricted prosthesis end (e.g., 10-12 mm) inserted into the vessel. Providing a sheath having a length that exceeds the length of the constricted portion of the prosthesis is generally acceptable, but is less desirable than providing a sheath of substantially the same length, or only slightly longer (e.g. by about 1 mm) than the constricted sheath length. The width of the tab member is preferably between about 2 and 3 mm. A narrow tab is generally preferred for feeding through the sheath body, since it takes less space away from that available for the prosthesis. In one example, the length of the slit 11 is about 1 mm. Providing a longer slit may cause the sheath material alongside the slit to open or flare and interfere with insertion into a vessel in some instances. The tab should have a length sufficient to feed through the delivery system and enable the user to grasp an end thereof. In one example, the tab length is about 8-16 cm.

Figure 12:
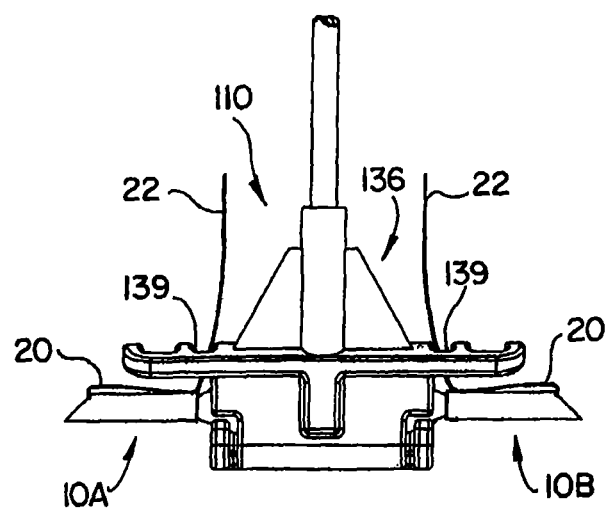
FIG. 12 is a side view of the prosthesis of FIG. 11 loaded into a delivery device for deployment.

FIG. 12 illustrates the sheathed prosthesis 200 loaded into delivery device 110. As shown in the figure and as described above, sheaths 10A, 10B are positioned to constrict the respective proximal and distal ends of the prosthesis. Retaining members 120, 136 of the delivery device are initially in the open, or spaced, position as shown in FIGS. 7-9 when the prosthesis and sheaths are loaded into the delivery device. Once the prosthesis and sheaths have been loaded into delivery device 110, retaining members 120, 136 are maneuvered into the closed position shown in FIG. 12, e.g., by manipulating the finger loops 117, 133 of the delivery device. An end 22 of each tab member 20 of the respective sheaths is threaded through an aperture 139 of retaining member 136.

Figure 13:
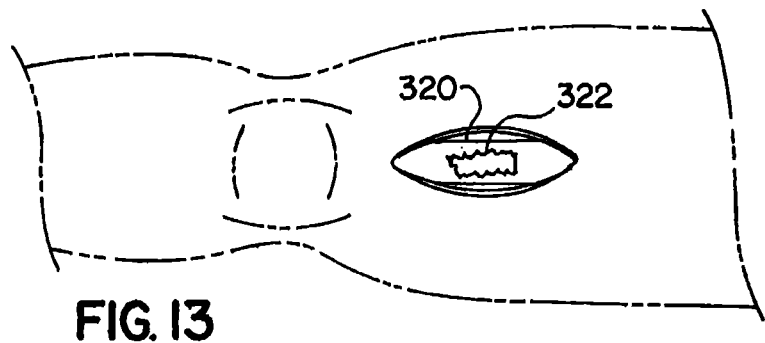
FIG. 13 illustrates a leg of a patient that has been opened to expose a damaged body vessel.
Figure 14:
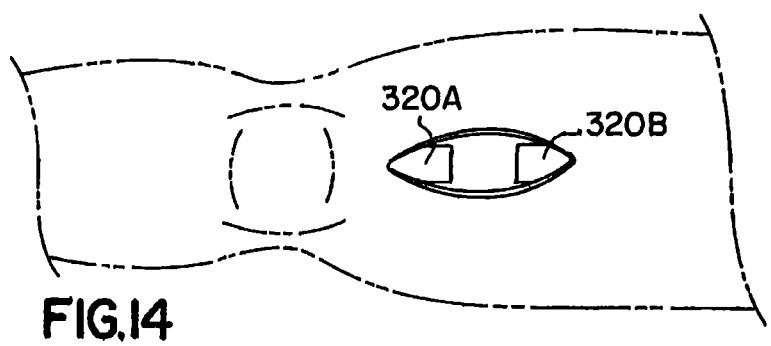
FIG. 14 illustrates the body vessel of FIG. 13, wherein the vessel has been cut into two end portions.

FIG. 13 depicts one example of a body vessel for deployment of a prosthesis, in this case a body vessel 320 in the leg of a patient. The body vessel 320 has previously been subjected to a traumatic episode, resulting in a portion 322 of body vessel 320 being torn away or otherwise severely damaged. Pre-surgery preparation has been applied to the leg and a trauma pathway has been formed therein in order to gain direct, open air, access to the body vessel and the damaged portion thereof. After clamping the body vessel 320 on both ends of the portion 322 to restrict blood flow temporarily, the body vessel 320 can be cut or transected by the clinician into two end portions 320A, 320B, as shown in FIG. 14. The transection may be at the damaged portion 322 of the blood vessel 320, and extend as far away as necessary from the damaged portion to remove unhealthy and/or unrepairable portions of the body vessel.

A prosthesis 200 is selected to have a longitudinal length sufficient to bridge the gap between the body vessel portions 320A, 320B, and a radial expanded cross-section sufficient to engage the inner walls of the body vessel portions. The prosthesis 200 having sheaths 10A, 10B in place at the respective distal ends of the prosthesis (FIG. 11) is loaded into delivery device 110. As shown in FIG. 12 and as described above, prosthesis 200 is captured between retaining members 120, 136 of the delivery device which have been maneuvered into the closed position as shown. In some examples, the prosthesis may be pre-loaded into the delivery device, so that the user need not carry out this loading step.

Figure 15:
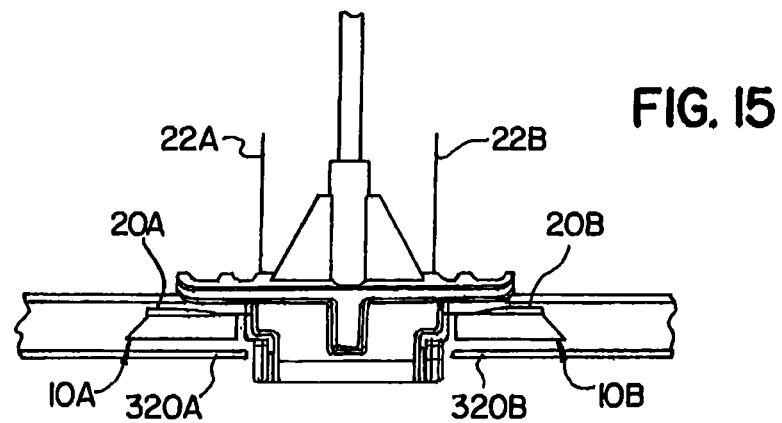
FIG. 15 illustrates the delivery device and the respective ends of the prosthesis as inserted into the vessel end portions of FIG. 14, prior to expansion of the prosthesis.

The distal end of delivery device 110 having the prosthesis loaded therein is maneuvered into the damaged leg portion shown in FIG. 15 through an open air opening as shown in FIGS. 13, 14. The respective ends of the prosthesis covered by sheaths 10A, 10B are inserted into respective vessel ends 320A and 320B. Typically, the ends are inserted to the maximum distance allowed by the retaining members (FIG. 15). In this event, the anchoring members of the prosthesis are in position to engage within the tissue upon expansion of the prosthesis. The vessel portion 320A may be manually pulled over sheath 10A. The delivery device 110 and the prosthesis 200 can be manipulated in order to introduce sheath 10B into the vessel portion 320B in similar fashion.

Respective ends 22A, 22B of tabs 20A, 20B are pulled to split the underlying sheath 10A, 10B. For vessels at a lesser depth in the leg, the ends 22A, 22B may be accessible to the physician. In this instance, the tabs may be pulled by hand. For deeper vessels, a needle holder, clamp, or like device may be used to pull the respective tabs in well-known fashion. Alternatively, a respective prosthesis end can be inserted into either vessel portion 320A or 320B, and the tab associated with that prosthesis end can be pulled. Then the opposite end of the prosthesis can be inserted into the other vessel end and its tab can be pulled. In this example, the anchoring members on the first end will keep the prosthesis engaged with the vessel end during manipulation to insert/deploy the second end. Since the vessels are elastic, they are often stretched slightly in order to properly engage the prosthesis. In some cases, it may be difficult to keep both vessel ends in position over the sheaths prior to pulling the tabs, and thus, the sequential insertion as described may be advantageous.

As tab ends 22A, 22B are sequentially pulled, the sheath body 12 is initially split from the pre-weakened slit portion 11 as described above, and thereafter entirely split along one side (FIG. 4 to FIG. 6). At this time the tab 20A, 20B remains attached to the remainder of the sheath body. Continued exertion of a pulling force on the tab causes the opened sheath body to pull away from the prosthesis and from the vessel.

Figure 16:
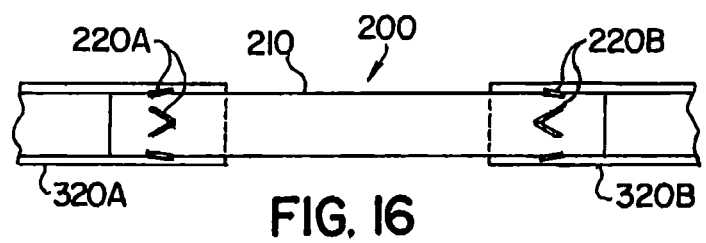
FIG. 16 illustrates the prosthesis deployed in the vessel in an expanded condition following removal of the sheaths.

Once relieved from the constraints imposed by sheaths 10A, 10B the prosthesis distal ends self-expand to the interior diameter of the vessel, or alternatively, to a diameter slightly greater (e.g., about 1-2 mm greater) than the interior diameter of the vessel. Upon self-expansion of the prosthesis, barbs 220A, 220B engage the interior vessel wall, as shown in FIG. 16. Upon deployment of the prosthesis, delivery device 110 may be opened and removed from the vessel. The vessel may be unclamped and/or untied to restore blood flow therethrough. Stent 206 is not shown in FIG. 16 to better illustrate the barbs. In addition, in some embodiments graft body 210 may overlie the stent, such that the stent would not be visible. As shown, the prosthesis 200 is fully deployed and expanded to interconnect the first and second vessel portions 320A, 320B of the body vessel 320 to form a conduit, e.g., for blood flow. As stated, prosthesis 200 can be adapted for permanent placement within the patient, thereby obviating a need for subsequent surgical intervention.

Although the sheath has been described in connection with its primary intended use in conjunction with a stent/graft device for repair of vascular trauma, those skilled in the art will appreciate that the sheath may also be used during repair of other traumatic conditions, such as trauma in other body vessels, as well as during bypass surgery. Additionally, the sheath may be utilized in other procedures where dual-tab sheaths are currently in use, such as during percutaneous placement procedures.

It is therefore intended that the foregoing detailed description be regarded as illustrative rather than limiting, and that it be understood that it is the following claims, including all equivalents, that are intended to define the spirit and scope of this invention.

The invention claimed is:

1. An assembly for open surgical repair of a damaged portion of a body vessel, the assembly comprising:
   a prosthesis having a first end and a second end, the prosthesis being expandable from a constricted condition wherein at least the first and second ends have a diameter less than a diameter of the body vessel at said damaged portion, to an expanded condition wherein the prosthesis ends engage an interior surface of said body vessel;
   a first splittable sheath for maintaining the prosthesis first end in said constricted condition, the first splittable sheath comprising a generally cylindrical body having a first end portion, a second end portion, a passageway extending therethrough, and an elongated tab member integral with the first splittable sheath, the tab member being engaged at said second end portion, said tab member positionable along said generally cylindrical body for initiating a splitting of said generally cylindrical body of said first splittable sheath from said first end portion toward said second end portion, wherein said first splittable sheath is disposed upon the first end of the prosthesis and wherein said splitting of said first splittable sheath extends from said first end of said prosthesis toward said second end of said prosthesis, and wherein the elongated tab member of the first splittable sheath is positioned along said generally cylindrical body such that when said generally cylindrical body is split, the elongated tab member comprises a twist; and
   a second splittable sheath for maintaining the prosthesis second end in said constricted condition, the second splittable sheath comprising a generally cylindrical body having a first end portion, a second end portion, a passageway extending therethrough, and an elongated tab member integral with the second splittable sheath, the tab member being engaged at said second end portion, said tab member positionable along said generally cylindrical body for initiating a splitting of said generally cylindrical body of said second splittable sheath from said first end portion toward said second end portion, wherein said second splittable sheath is disposed upon the second end of the prosthesis and wherein said splitting of said second splittable sheath extends from said second end of said prosthesis toward said first end of said prosthesis, wherein at least one of said sheaths has a length of about 10-12 mm.

2. The assembly of claim 1, wherein said prosthesis includes one or more anchoring members at said first and second ends for anchoring said ends in said body vessel interior surface.

3. The assembly claim 1, wherein said prosthesis comprises a supporting structure having a graft body disposed along a surface of the supporting structure.

4. The assembly of claim 1, wherein the first end portion of at least one of said splittable sheaths is pre-weakened for initiating said splitting at said first end portion.

5. The assembly of claim 4, wherein the first end portion of each of said first and second splittable sheaths is pre-weakened for initiating said splitting at said pre-weakened first end portion, said pre-weakening comprising a slit at said first end portion of said generally cylindrical body.

6. The assembly of claim 1, wherein said elongated tab member of said first splittable sheath is extendable from an initial position at said engagement with said second end portion through said passageway to an intermediate position wherein an end portion of said tab member is extendable beyond said first end portion; said elongated tab member being further extendable from said intermediate position to a deployment position wherein said end portion is extendable beyond said second end portion of said first splittable sheath.

7. The assembly of claim 6, wherein said elongated tab member of said second splittable sheath is extendable from an initial position at said engagement with said second end portion through said passageway to an intermediate position wherein an end portion of said tab member of said second sheath is extendable beyond said first end portion; said elongated tab member being further extendable along an outer surface of said generally cylindrical body from said intermediate position to a deployment position wherein said end portion of said tab member end is extendable beyond said second end portion of said second splittable sheath.

8. The assembly of claim 1, wherein at least one of said sheaths is formed of PTFE.

9. The assembly of claim 1, further comprising a delivery device for said prosthesis, said prosthesis and first and second splittable sheaths being loaded into said device for delivery to said damaged body vessel portion.

10. An assembly for open surgical repair of a damaged portion of a body vessel, the assembly comprising:
a prosthesis having a first end and a second end, the prosthesis being expandable from a constricted condition wherein at least the first and second ends have a diameter less than a diameter of the body vessel at said damaged portion, to an expanded condition wherein the prosthesis ends engage an interior surface of said body vessel;
a first splittable sheath for maintaining the prosthesis first end in said constricted condition, the first splittable sheath comprising a generally cylindrical body having a first end portion, a second end portion, a passageway extending therethrough, and an elongated tab member extending from the second end portion of the first splittable sheath, said tab member positionable along said generally cylindrical body for initiating a splitting of said generally cylindrical body of said first splittable sheath from said first end portion toward said second end portion, wherein said first splittable sheath is disposed upon the first end of the prosthesis and wherein said splitting of said first splittable sheath extends from said first end of said prosthesis toward said second end of said prosthesis, and wherein the elongated tab member of the first splittable sheath is positioned along said generally cylindrical body such that when said generally cylindrical body is split, the elongated tab member comprises a twist; and a second splittable sheath for maintaining the prosthesis second end in said constricted condition, the second splittable sheath being spaced apart from the first splittable sheath to define an intermediate length of the prosthesis which is between the first splittable sheath the second splittable sheath and is unconstrained by the first splittable sheath and the second splittable sheath, the second splittable sheath comprising a generally cylindrical body having a first end portion, a second end portion, a passageway extending therethrough, and an elongated tab member extending from the second end portion of the second splittable sheath, said tab member positionable along said generally cylindrical body for initiating a splitting of said generally cylindrical body of said second splittable sheath from said first end portion toward said second end portion, wherein said second splittable sheath is disposed upon the second end of the prosthesis and wherein said splitting of said second splittable sheath extends from said second end of said prosthesis toward said first end of said prosthesis.

11. The assembly of claim 10, wherein said prosthesis includes one or more anchoring members at said first and second ends for anchoring said ends in said body vessel interior surface.

12. The assembly of claim 11, wherein the first end portion of at least one of said splittable sheaths is pre-weakened for initiating said splitting at said first end portion.

13. The assembly of claim 12, wherein the first end portion of each of said first and second splittable sheaths is pre-weakened for initiating said splitting at said pre-weakened first end portion, said pre-weakening comprising a slit at said first end portion of said generally cylindrical body.

14. The assembly claim 10, wherein said prosthesis comprises a supporting structure having a graft body disposed along a surface of the supporting structure.

15. The assembly of claim 10, wherein said elongated tab member of said first splittable sheath is extendable from an initial position at said engagement with said second end portion through said passageway to an intermediate position wherein an extended end of said tab member is extendable beyond said first end portion; said elongated tab member being further extendable from said intermediate position to a deployment position wherein said extended end is extendable beyond said second end portion of said first splittable sheath.

16. The assembly of claim 15, wherein said elongated tab member of said second splittable sheath is extendable from an initial position at said engagement with said second end portion through said passageway to an intermediate position wherein an extended end of said tab member of said second sheath is extendable beyond said first end portion; said elongated tab member being further extendable along an outer surface of said generally cylindrical body from said intermediate position to a deployment position wherein said extended end of said tab member end is extendable beyond said second end portion.

17. The assembly of claim 10, wherein at least one of said sheaths is formed of PTFE.

18. The assembly of claim 10, further comprising a delivery device for said prosthesis, said prosthesis and first and second splittable sheaths being loaded into said device for delivery to said damaged body vessel portion.

19. An assembly for open surgical repair of a damaged portion of a body vessel, the assembly comprising:
a prosthesis having a first end and a second end, the prosthesis being expandable from a constricted condition wherein at least the first and second ends have a diameter less than a diameter of the body vessel at said damaged portion, to an expanded condition wherein the prosthesis ends engage an interior surface of said body vessel;

a splittable sheath for maintaining the prosthesis first end in said constricted condition, the splittable sheath comprising a generally cylindrical body having a first end portion, a second end portion, a passageway extending therethrough, and an elongated tab member engaged at said second end portion, said tab member positionable along said generally cylindrical body for initiating a splitting of said generally cylindrical body of said splittable sheath from said first end portion toward said second end portion, wherein said splittable sheath is disposed upon the first end of the prosthesis, wherein said splitting of said splittable sheath extends from said first end of said prosthesis toward said second end of said prosthesis, and wherein the elongated tab member is positioned along said generally cylindrical body such that when said generally cylindrical body is split, the elongated tab member comprises a twist.

20. The assembly of claim 19, wherein the elongated tab member is positioned along said generally cylindrical body such that the elongated tab member comprises a first fold at the second end portion of the generally cylindrical body and a second fold at the first end portion of the generally cylindrical body.

* * * * *